(12) United States Patent
Jago et al.

(10) Patent No.: US 6,224,552 B1
(45) Date of Patent: May 1, 2001

(54) ULTRASONIC DIAGNOSTIC IMAGING SYSTEM WITH REDUCED SPATIAL COMPOUNDING SEAM ARTIFACTS

(75) Inventors: James R. Jago, Seattle; Daniel C. Schmiesing, Granite Falls; Robert R. Entrekin, Kirkland, all of WA (US)

(73) Assignee: ATL Ultrasound, Bothell, WA (US)

( * ) Notice: Subject to any disclaimer, the term of this patent is extended or adjusted under 35 U.S.C. 154(b) by 0 days.

(21) Appl. No.: 09/335,157

(22) Filed: Jun. 17, 1999

Related U.S. Application Data
(60) Provisional application No. 60/102,923, filed on Oct. 1, 1998.

(51) Int. Cl.[7] .................................................. A61B 8/00
(52) U.S. Cl. ........................................... 600/437; 600/443
(58) Field of Search .................................. 600/447, 449, 600/437, 443, 444, 438

(56) References Cited

U.S. PATENT DOCUMENTS

| | | |
|---|---|---|
| 4,070,905 | 1/1978 | Kossoff . |
| 4,159,462 | 6/1979 | Rocha et al. . |
| 4,537,199 * | 8/1985 | Muranaka .......................... 600/437 |
| 4,649,927 | 3/1987 | Fehr et al. . |
| 4,751,846 | 6/1988 | Dousse . |
| 5,538,004 | 7/1996 | Bamber . |
| 5,566,674 | 10/1996 | Weng . |
| 5,575,286 | 11/1996 | Weng et al. . |
| 5,623,929 | 4/1997 | Weng . |
| 5,653,235 | 8/1997 | Teo . |
| 5,655,535 | 8/1997 | Teo et al. . |
| 5,782,766 | 7/1998 | Weng et al. . |
| 5,908,390 | 6/1999 | Matsushima . |
| 5,993,392 * | 11/1999 | Roundhill et al. .................. 600/447 |
| 6,045,506 * | 4/2000 | Hossack ............................. 600/443 |

FOREIGN PATENT DOCUMENTS 0 815 793   1/1998   (EP) .

OTHER PUBLICATIONS

Feigenbaum, Echocardiography, Lea & Febiger, 1976 at pp 32–34, Philadelphia, PA.

Carpenter et al., Technical Note—A Multimode Real Time Scanner, Ultrsound in Med. & Biol., vol. 6, pp 279–284, Pergamon Press Ltd. 1980, Great Britain.

Berson et al., Compound Scanning With a Electrically Steered Beam, Ultrasonic Imaging 3, pp 303–308, Academic Press, Inc. 1981.

Shattuck et al., Compound Scanning With a Phased Array, Ultrasonic Imaging 4, pp 93–107, Academic Press, Inc. 1982.

Jesperson et al., Multi–Angle Compound Imaging, Ultrasonic Imaging 20, pp 81–102, Dynamedia, Inc. 1998.

* cited by examiner

*Primary Examiner*—Marvin M. Lateef
*Assistant Examiner*—Maulin Patel
(74) *Attorney, Agent, or Firm*—W. Brinton Yorks, Jr.

(57) ABSTRACT

An ultrasonic diagnostic imaging system produces spatially compounded images by combining component frames acquired from different look directions. Different regions of the spatially compounded images are formed by different numbers of overlapping component frames. Seam artifacts at the boundaries of the regions are reduced by processing the component frames to maintain a common signal and noise characteristic, varying the transmit pulse amplitude or the receiver gain, spatially aligning component frames at the boundaries, or weighting scan lines less heavily at the seam boundaries.

24 Claims, 4 Drawing Sheets

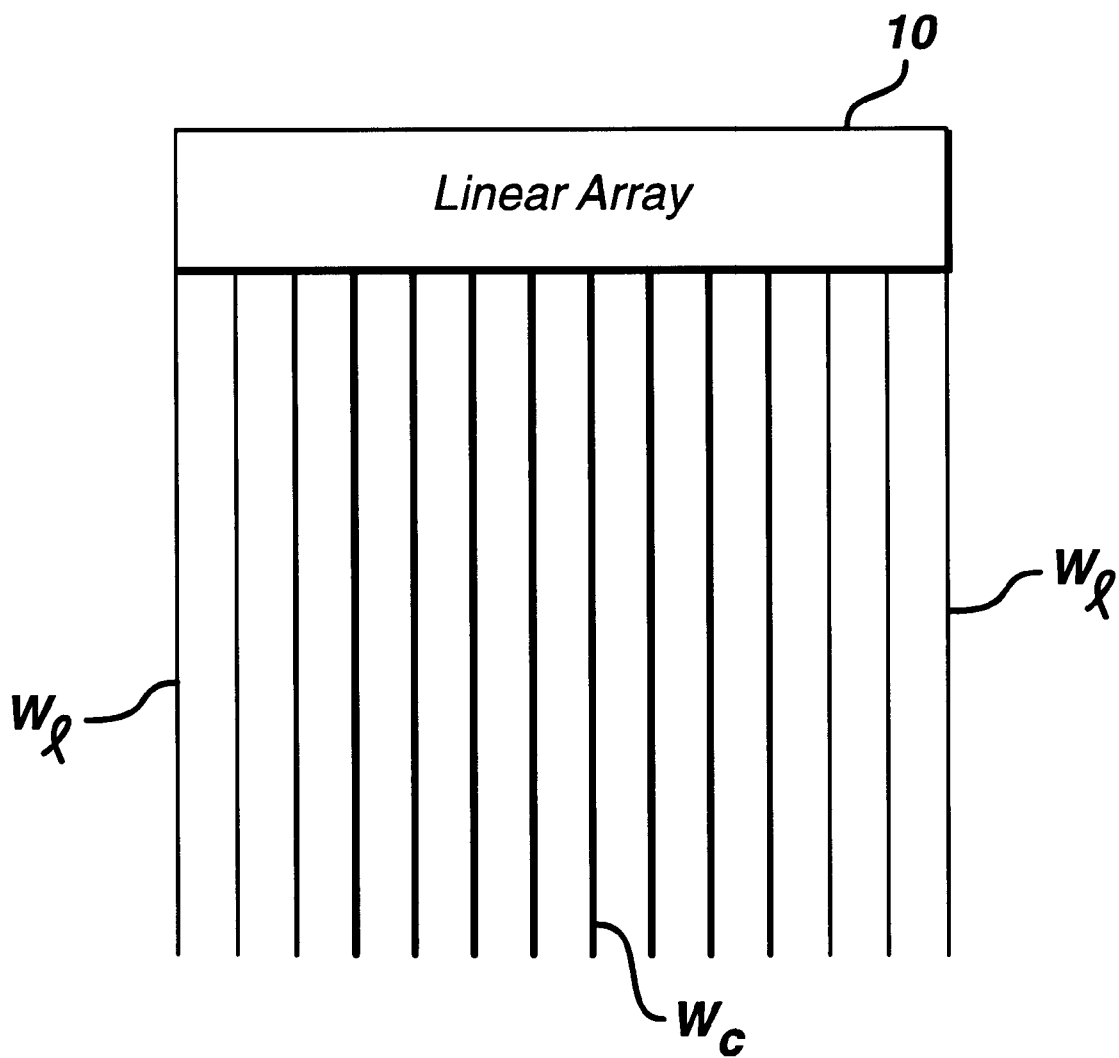

ULTRASONIC DIAGNOSTIC IMAGING SYSTEM WITH REDUCED SPATIAL COMPOUNDING SEAM ARTIFACTS

This application claims the benefit of Provisional U.S. Patent Application Ser. No. 60/102,923, filed Oct. 1, 1998.

This invention relates to ultrasonic diagnostic imaging systems and, in particular, to ultrasonic diagnostic imaging systems which produce spatially compounded images with reduced seam artifacts.

Spatial compounding is an imaging technique in which a number of ultrasound images of a given target that have been obtained from multiple vantage points or angles are combined into a single compounded image by combining the data received from each point in the compound image target which has been received from each angle. Examples of spatial compounding may be found in U.S. Pat. Nos. 4,649,927; 4,319,489; and 4,159,462. Real time spatial compound imaging is performed by rapidly acquiring a series of partially overlapping component image frames from substantially independent spatial directions, utilizing an array transducer to implement electronic beam steering and/or electronic translation of the component frames. The component frames are combined into a compound image by summation, averaging, peak detection, or other combinational means. The acquisition sequence and formation of compound images are repeated continuously at a rate limited by the acquisition frame rate, that is, the time required to acquire the full complement of scanlines over the selected width and depth of imaging.

The compounded image typically shows lower speckle and better specular reflector delineation than conventional ultrasound images from a single viewpoint. Speckle is reduced (i.e. speckle signal to noise ratio is improved) by the square root of N in a compound image with N component frames, provided that the component frames used to create the compound image are substantially independent and are averaged. Several criteria can be used to determine the degree of independence of the component frames (see, e.g., O'Donnell et al. in IEEE Trans. UFFC v.35, no.4, pp 470–76 (1988)). In practice, for spatial compound imaging with a steered linear array, this implies a minimum steering angle between component frames. This minimum angle is typically on the order of several degrees.

The second way that spatial compound scanning improves image quality is by improving the acquisition of specular interfaces. For example, a curved bone-soft tissue interface produces a strong echo when the ultrasound beam is exactly perpendicular to the interface, and a very weak echo when the beam is only a few degrees off perpendicular. These interfaces are often curved, and with conventional scanning only a small portion of the interface is visible. Spatial compound scanning acquires views of the interface from many different angles, making the curved interface visible and continuous over a larger field of view. Greater angular diversity generally improves the continuity of specular targets. However, the angular diversity available is limited by the acceptance angle of the transducer array elements. The acceptance angle depends on the transducer array element pitch, frequency, and construction methods.

One of the problems that can arise when image lines from a plurality of look directions are acquired by a transducer is that all points in the ultimate compound image may not be insonified by the same number of differently steered beams. Consequently, different points or pixels in the compound image may be formed with different amounts of acquired data. Generally points in the central near field of the image will be formed from the greatest number of acquired echoes, while points at the lateral extremes and greater depths of the image are formed with fewer echoes, as fewer beams of different look directions are conveniently steered to those locations. While the processing of a compound image will usually take this uneven distribution of echoes into account when the echoes are summed by normalizing the sums as a function of the number of echoes or component pixels used to form the compound image pixel, the boundaries or seams between image regions of greater and lesser numbers of overlapping echoes can still be apparent in the image. Accordingly it is desirable to reduce these seam appearances in a spatially compounded image.

In accordance with the principles of the present invention, several techniques are described for reducing seam artifacts in a spatially compounded image. Transmit, receive or processing adjustments can be made to ensure that all regions in the compounded image have the same brightness. For example, compensation can be made for changes in echo amplitude due to beam steering or due to variable transmit or receive aperture size. Receive gain compensation, preferably automatic gain compensation, can be used to overcome conditions of varying attenuation of an echo signal. Seams due to motion effects can be reduced by resampling the echo data as a function of the sensing of motional effects. Seam blending, by which echo or pixel data in the vicinity of a seam is weighted, can be used to reduce seam artifacts in a compound image. Preferably, a number of these techniques are applied to the same image so that seam artifacts arising from a variety of causes can be reduced.

In the drawings:

FIG. 4 illustrates weighting of echo information to seamlessly blend echoes in the vicinity of a compound image seam.

Figure 1:
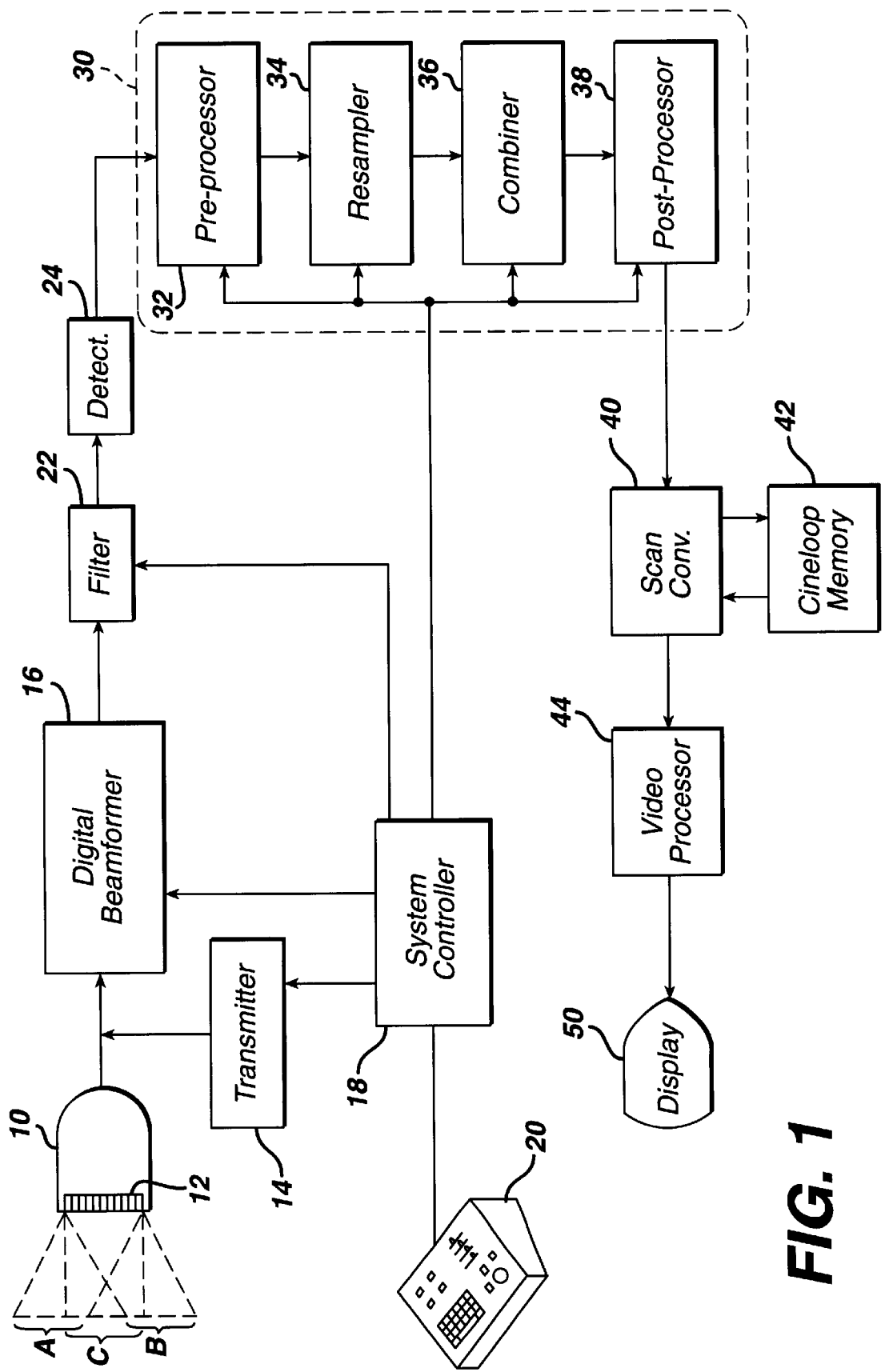
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown. A scanhead 10 including an array transducer 12 transmits beams at different angles over an image field denoted by the dashed rectangle and parallelograms. Three groups of scanlines are indicated in the drawing, labeled A, B, and C with each group being steered at a different angle relative to the scanhead. The transmission of the beams is controlled by a transmitter 14 which controls the phasing and time of actuation of each of the elements of the array transducer so as to transmit each beam from a predetermined origin along the array and at a predetermined angle. The echoes returned from along each scanline are received by the elements of the array, digitized as by analog to digital conversion, and coupled to a digital beamformer 16. The digital beamformer delays and sums the echoes from the array elements to form a sequence of focused, coherent digital echo samples along each scanline. The transmitter 14 and beamformer 16 are operated under control of a system controller 18, which in turn is responsive to the settings of controls on a user interface 20 operated by the user of the ultrasound system. The system controller controls the transmitter to transmit the desired number of scanline groups at the desired angles, transmit energies and frequencies. The system controller also controls the digital beamformer to properly delay and combine the received echo signals for the apertures and image depths used.

The scanline echo signals are filtered by a programmable digital filter 22, which defines the band of frequencies of interest. When imaging harmonic contrast agents or performing tissue harmonic imaging the passband of the filter 22 is set to pass harmonics of the transmit band. The filtered signals are then detected by a detector 24. In a preferred embodiment the filter and detector include multiple filters and detectors so that the received signals may be separated into multiple passbands, individually detected and recombined to reduce image speckle by frequency compounding. For B mode imaging the detector 24 will perform amplitude detection of the echo signal envelope. For Doppler imaging ensembles of echoes are assembled for each point in the image and are Doppler processed to estimate the Doppler shift or Doppler power intensity.

In accordance with the principles of the present invention the digital echo signals are processed by spatial compounding in a processor 30. The digital echo signals are initially pre-processed by a preprocessor 32. The pre-processor 32 can preweight the signal samples if desired with a weighting factor. The samples can be preweighted with a weighting factor that is a function of the number of component frames used to form a particular compound image. The pre-processor can also weight edge lines that are at the edge of one overlapping image so as to smooth the transitions where the number of samples or images which are compounded changes. The pre-processed signal samples may then undergo a resampling in a resampler 34. The resampler 34 can spatially realign the estimates of one component frame or to the pixels of the display space.

After resampling the image frames are compounded by a combiner 36. Combining may comprise summation, averaging, peak detection, or other combinational means. The samples being combined may also be weighted prior to combining in this step of the process. Finally, post-processing is performed by a post-processor 38. The post-processor normalizes the combined values to a display range of values. Post-processing can be most easily implemented by look-up tables and can simultaneously perform compression and mapping of the range of compounded values to a range of values suitable for display of the compounded image.

The compounding process may be performed in estimate data space or in display pixel space. In a preferred embodiment scan conversion is done following the compounding process by a scan converter 40. The compound images may be stored in a Cineloop® memory 42 in either estimate or display pixel form. If stored in estimate form the images may be scan converted when replayed from the Cineloop memory for display. The scan converter and Cineloop memory may also be used to render three dimensional presentations of the spatially compounded images as described in U.S. Pat Nos. 5,485,842 and 5,860,924. Following scan conversion the spatially compounded images are processed for display by a video processor 44 and displayed on an image display 50.

Figure 2:
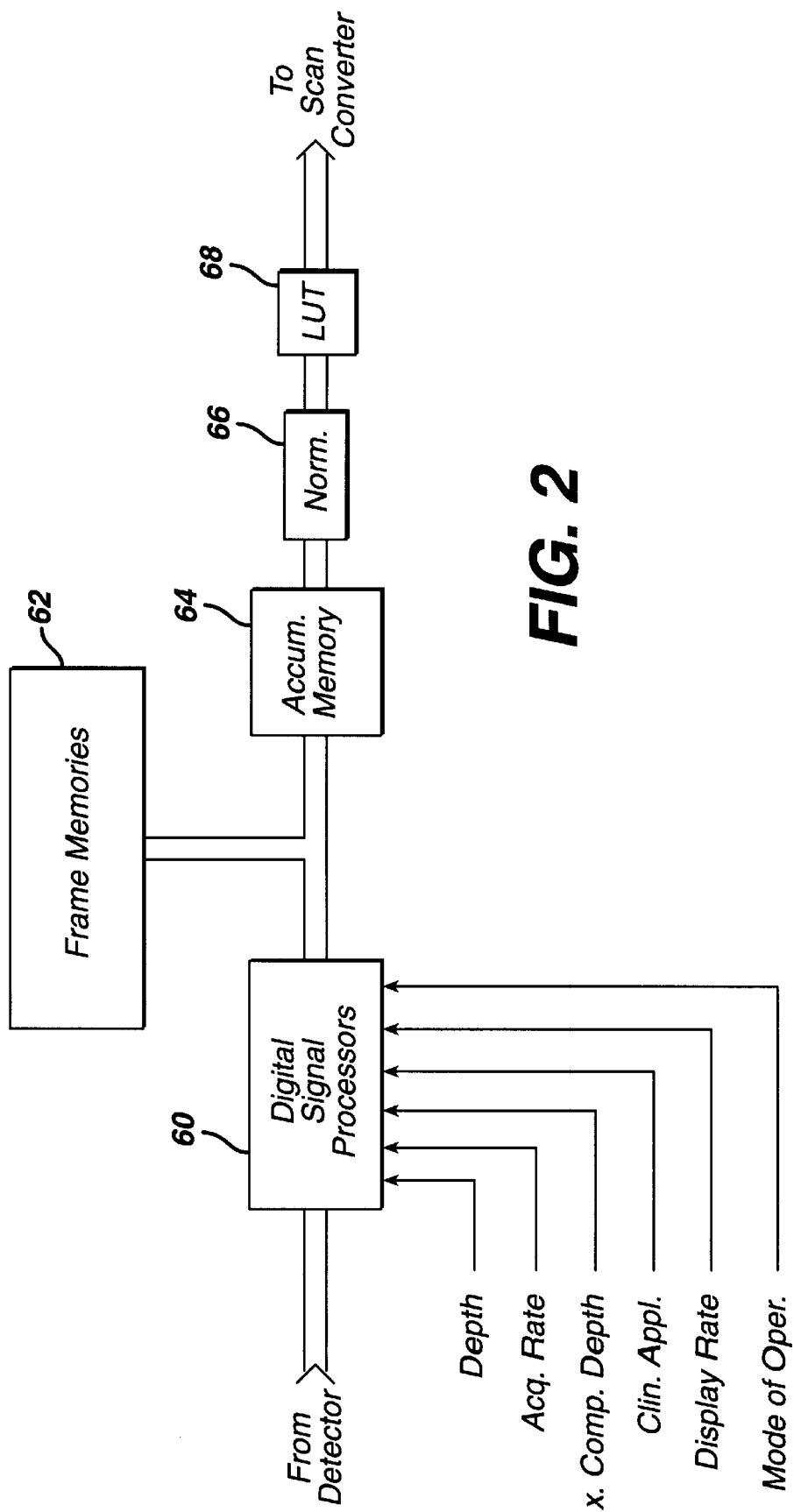
FIG. 2 illustrates in block diagram form a preferred implementation of the spatial compounding processor of FIG. 1.

FIG. 2 illustrates a preferred implementation of the spatial compounding processor 30 of FIG. 1. The processor 30 is preferably implemented by one or more digital signal processors 60 which process the image data in various ways. The digital signal processors 60 can weight the received image data and can resample the image data to spatially align pixels from frame to frame, for instance. The digital signal processors 60 direct the processed image frames to a plurality of frame memories 62 which buffer the individual image frames. The number of image frames capable of being stored by the frame memories 62 is preferably at least equal to the maximum number of image frames to be compounded such as sixteen frames. In accordance with the principles of the present invention, the digital signal processors are responsive to control parameters including image display depth, depth of region of greatest compounding, clinical application, compound display rate, mode of operation, and acquisition rate for determining the number of images to compound at a given instant in time. The digital signal processors select component frames stored in the frame memories 62 for assembly as a compound image in accumulator memory 64. The compounded image formed in the accumulator memory 64 is weighted or mapped by a normalization circuit 66, then compressed to the desired number of display bits and, if desired, remapped by a lookup table (LUT) 68. The fully processed compounded image is then transmitted to the scan converter for formatting and display.

Figure 3B:
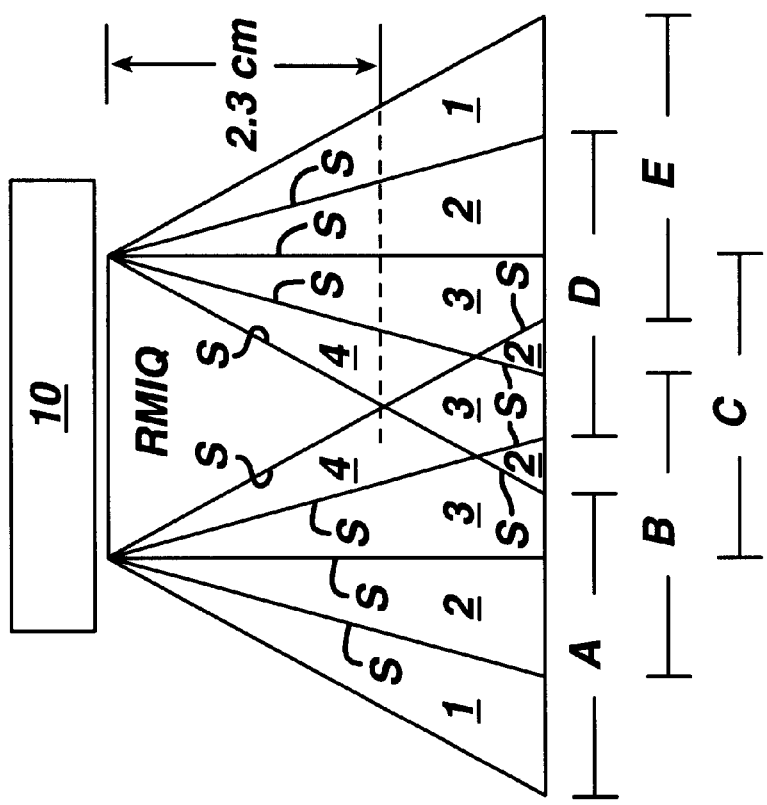
FIGS. 3a and 3b illustrate the overlap of different amount of echo information in steered linear compound scan formats.
Figure 3A:
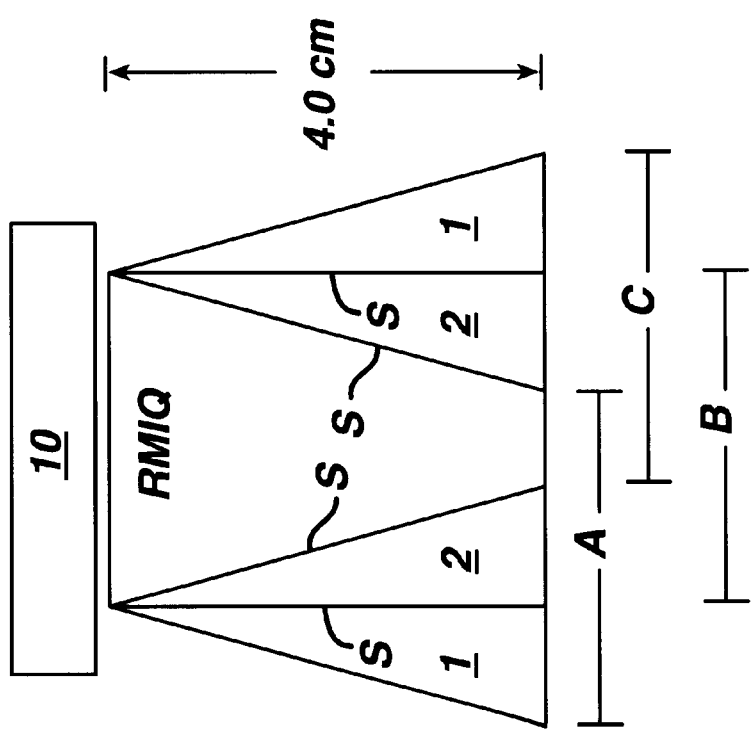

Compound scanning with a steered linear array results in a pattern of overlapping component frames such that the region of maximum image quality (RMIQ) where all N frames overlap is an inverted triangular region with its base at the top of the compound image. With other scanning geometries such as overlapping phased array frames emanating from different points of the array, the RMIQ will exhibit a correspondingly different shape. This is illustrated by FIGS. 3a and 3b, which show two different compound scan geometries, each consisting of several partially overlapping steered linear component frames scanned from a linear array scanhead 10. For visual clarity, the minimum steering angle was chosen as 15° between component frames. FIG. 3a shows three component frames A, B, and C which are compounded. On either side of the RMIQ region the number of overlapping frames decreases spatially, with only two frames overlapping in the regions designated 2 and single frames present in the regions designated 1. This means that a particular point in the compounded image may only receive contributions from a sub-set of the component frames, depending on whether a component frame has data at that point. The transitions between these numbered regions, which will hereafter be referred to as "seams", occur at the edges S of each component frame and therefore represent a sudden change in the number of frames being summed.

FIG. 3b shows an image which compounds five component frames A, B, C, D and E. The regions on either side of and below the RMIQ are designated by the number of frames which overlap and hence are compounded in each region of the compound image. These drawings show that increasing the number of frames in the compound image decreases the size of the RMIQ and increases the number of regions combining different numbers of frames, and hence the number of seams S in the image.

A normalization map is typically applied after summation that compensates for the fact that these regions represent an averaging of differing numbers of frames. For example, if N frames are to be averaged at a particular point, then data from these frames at that point would be summed and then normalized by scaling with 1/N. This normalization map is fixed for a particular compounding geometry and therefore can be pre-computed and need not be updated in real time.

One of the problems encountered in spatial compounding, and in particular real-time compounding, is that these seams S at the edges of the component frames can often be seen. The seams may become visible due to two main causes:

1) If, for any reason, the echo data contributed to the compounded image by points at the edge of a particular component frame do not match the echo data already obtained from the corresponding points within the other component frames, the averaging of these data will not generate the expected compounded result and the seam at the edge of the frame will become noticeable. There are several reasons why the echo data at the edge of one component frame may not match data from other component frames:

a) The echo data may have different amplitudes because the ultrasound beams of the component frames are obtained from different steering directions.

b) For linear arrays the echo data may have different amplitudes because beams close to the edges of the frames use smaller apertures.

c) The echo data may have different amplitudes because the ultrasound beams of the component frames have gone through different amounts of attenuation in the target medium, for example because of the varying attenuation coefficients of different tissue types or because of varying acoustical coupling along the array.

d) The echo data may have been returned by different targets because the tissue and/or probe have moved during acquisition of the component frames.

2) Since the degree of speckle reduction increases with the number of compounded frames, the appearance of speckle may be different on different sides of the seams.

In accordance with the principles of the present invention, seam artifacts arising from one or more of these sources are reduced as follows:

Correction for Signal Amplitude Variation due to Beamforming

Echo signal amplitude variations described in 1)a) and b) above are due solely to beamforming effects and can therefore be predicted and/or measured to good accuracy and correction factors determined. For example, beam steering at angles away from normal to the array reduces echo signal amplitude because of the combined effects of limited array element directivity and reduced effective aperture size. For linear arrays, echoes from beams near the edges of the frame have reduced amplitude because these beams require array elements beyond the physical extent of the transducer array. These reductions in echo amplitude can be offset by transmitting beams with greater amplitude pulses at steep steering angles and at the periphery of the transducer aperture. Preferably, the corrections for these effects are applied on transmit by the transmitter 14 so that all component frames have the same signal-to-noise ratio. Alternatively, part or all of the correction may be applied on receive by increasing system gain (amplification) during these steep angle or aperture edge conditions, in which case it would be preferable to also adjust the dynamic range of the corrected data at the logarithmic compression stage so that all component frames have the same noise level.

Correction for Signal Amplitude Variation due to Target

Signal amplitude variations arising from varying attenuation as described in 1)c) above are harder to predict since they are determined by the target. However techniques exist for data-dependent automatic gain compensation (AGC) which can help to reduce the extent of signal amplitude variations caused by target attenuation. A preferred technique, which continually adjusts the gain of the receiver as a function of echoes received along the scanline, is shown in U.S. Pat. No. 5,697,372.

Correction for Motion Induced Effects

Correction for motion effects of 1)d) and a consequent reduction in seam visibility is possible if estimates of motion can be determined for both the target and the probe, either based on correlation of the image data itself or, in the case of probe movement, mechanical or electronic motion sensors. Correction of the echo data is performed by the resampler 34 in FIG. 1 as more fully described in copending patent application Ser. No. 09/335,059, entitled "ULTRASONIC DIAGNOSTIC IMAGING SYSTEM WITH BLURRING-CORRECTED SPATIAL COMPOUNDING."

Seam Blending

A further technique for reducing the visibility of seams caused by motion, or indeed for reducing residual seams caused by any other mechanism which may not have been fully eliminated by other methods (including but not restricted to those listed above), is to alter the compounding algorithm such that there is no longer a sudden discontinuity at the edges between regions of differing amounts of frame overlap. For example, one can weight the amplitude of scan lines in a component frame before compounding, depending on how close the scan lines are to the edge of a frame, the amplitude being for example fractionally small for the very first and last scan lines in a frame as shown in FIG. 4. In the linear scan format shown in this drawing, scan lines near the center of the image are more heavily weighted by weighting factor $w_c$ as indicated by the more heavily drawn scan lines at the center of the image. On the lateral sides of the image, the scan lines are more lightly weighted by weighting factor $w_l$ as indicated by the more lightly drawn scan lines at the lateral sides of the image. This amplitude weighting is preferably applied after the other signal amplitude corrections discussed above had been applied. After compounding of multiple frames for which this kind of processing had been applied, there is a more gradual transition between regions of differing amounts of frame overlap and seams between these regions become less visible.

The normalization map that compensates for the fact that different regions in the compounded image represent a summation of differing numbers of frames would need to be modified to account for the reduced amplitude of frames close to the edges. However this mapping is still fixed for a particular compounding geometry and therefore can be pre-computed and need not updated in real time.

What is claimed is:

1. An ultrasonic diagnostic imaging system for producing spatially compounded images, including an array transducer which is operated to acquire component frames at a plurality of different look directions, and a compound image processor comprising:

a compound image memory for storing combined component frames which form a spatially compounded image in which different regions of said compounded image are formed from contributions from different numbers of component frames; and means for processing said component frames to exhibit substantially indistinguishable seams at the boundaries of adjoining regions.

2. The ultrasonic diagnostic imaging system of claim 1, wherein said means for processing comprises means for processing said component frames to exhibit substantially the same signal and noise characteristic at the seam boundary.

3. The ultrasonic diagnostic imaging system of claim 2, wherein said means for processing comprises a transmitter, coupled to said array transducer, which transmits acoustic energy of a level which is a function of at least one of transmit beam steering angle and location of the beam relative to the center of the array transducer.

4. The ultrasonic diagnostic imaging system of claim 2, wherein said means for processing comprises a receiver, coupled to said array transducer, which amplifies received scan lines by a gain factor which is a function of at least one of beam steering angle and location of the scan line relative to the center of the array transducer.

5. The ultrasonic diagnostic imaging system of claim 4, wherein said receiver further exhibits a dynamic range adjusted in accordance with said gain factor in order to achieve a constant noise level.

6. The ultrasonic diagnostic imaging system of claim 1, wherein said means for processing comprises a gain control circuit responsive to received echo signals for reducing the extent of signal amplitude variations caused by attenuation of an imaging target.

7. The ultrasonic diagnostic imaging system of claim 6, wherein said gain control circuit applies a gain factor to received echo signals which is a function of the amplitude of received echo signals.

8. The ultrasonic diagnostic imaging system of claim 1, wherein said means for processing comprises means for spatially aligning two component frames which overlap on one side of a boundary of adjoining regions.

9. The ultrasonic diagnostic imaging system of claim 8, wherein said means for spatially aligning comprises means for correlating the data of said two component frames.

10. The ultrasonic diagnostic imaging system of claim 8, wherein said means for spatially aligning comprises:
    means for estimating motion from said data of said two component frames; and
    means for aligning said two component frames on the basis of estimated motion.

11. The ultrasonic diagnostic imaging system of claim 1, wherein said means for processing comprises means for weighting the scanline data of a component frame at the boundary of adjoining regions.

12. The ultrasonic diagnostic imaging system of claim 11, wherein said scanline data is weighted less at a boundary of adjoining regions than at other points in said component frame.

13. The ultrasonic diagnostic imaging system of claim 12, wherein the scanline data of said component frame is weighted progressively less from the center of said component frame to the boundary of said component frame.

14. An ultrasonic diagnostic imaging system for producing spatially compounded images, including an array transducer which is operated to acquire component frames at a plurality of different look directions, comprising:
    a compound image memory for storing combined component frames which form a spatially compounded image in which different regions of said compounded image are formed from contributions from different numbers of component frames; and
    a processor which processes said component frames to exhibit substantially indistinguishable seams at the boundaries of adjoining regions by one or more of the following operations:
    processing said component frames to exhibit substantially the same signal and noise characteristic;
    transmitting acoustic energy of a level which is a function of at least one of transmit beam steering angle and location of the beam relative to the center of the array transducer;
    amplifying received scan lines by a gain factor which is a function of at least one of beam steering angle and location of the scan line relative to the center of the array transducer;
    applying a gain factor to received echo signals which is a function of the amplitude of received echo signals;
    spatially aligning two component frames which overlap on one side of a boundary of adjoining regions; and
    weighting the scanline data of a component frame at the boundary of adjoining regions.

15. A method for reducing seam artifacts at component frame boundaries in a spatially compounded ultrasonic image comprising the steps of:
    acquiring component frames of a spatially compounded image;
    processing one or more of said component frames to reduce seam artifacts by at least one of the operations of
        processing said component frames to exhibit substantially the same signal and noise characteristic;
        transmitting acoustic energy of a level which is a function of at least one of transmit beam steering angle and location of the beam relative to the center of the array transducer;
        amplifying received scan lines by a gain factor which is a function of at least one of beam steering angle and location of the scan line relative to the center of the array transducer;
        applying a gain factor to received echo signals which is a function of the amplitude of received echo signals;
        spatially aligning two component frames which overlap on one side of a boundary of adjoining regions; and
        weighting the scanline data of a component frame at the boundary of adjoining regions; and
    combining said component frames to form a spatially compounded image in which different regions of said compounded image are formed from contributions from different numbers of component frames.

16. The method of claim 15, further comprising the step of normalizing the image data of said spatially compounded image on the basis of the number of said component frames.

17. The method of claim 15, further comprising the step of normalizing the image data of said spatially compounded image, wherein the normalization incorporates the weights applied to each of the component frames.

18. A method for reducing seam artifacts at boundaries of regions in a spatially compounded ultrasonic image having image points for which image data has been acquired from different numbers of look directions comprising the steps of:
    acquiring image data from an ultrasonic image field from a plurality of different look directions, wherein adjacent regions of the image field have points for which image data has been acquired from a different number of look directions;
    processing the image data at the boundaries of the adjacent regions to reduce seam artifacts in a spatially compounded image which includes image data from the adjacent regions; and
    combining image data received from points in the image field which have been received from a plurality of different look directions to produce a spatially compounded ultrasonic image.

19. The method of claim 18, wherein processing further comprises:
    processing image data of the adjacent regions to exhibit substantially the same signal and noise characteristic.

20. The method of claim 18, wherein acquiring further comprises:

transmitting steered beams over an ultrasonic image field by an array transducer; and transmitting acoustic energy of a level which is a function of at least one of transmit beam steering angle and location of the beam relative to the center of the array transducer.

21. The method of claim 18, wherein acquiring further comprises transmitting steered beams over an ultrasonic image field by an array transducer; and wherein processing further comprises:

amplifying received image data signals by a gain factor which is a function of at least one of beam steering angle and location of the image data relative to the center of the array transducer.

22. The method of claim 18, wherein processing further comprises:

applying a gain factor to received image data signals which is a function of the amplitude of received echo signals.

23. The method of claim 18, wherein processing further comprises:

spatially aligning image data from different look directions which corresponds to the same image point in the image field on one side of a boundary of adjacent regions.

24. The method of claim 18, wherein processing further comprises:

weighting the image data of image points at the boundary of adjacent regions.

* * * * *